United States Patent
Ramotowski

(10) Patent No.: US 8,820,155 B2
(45) Date of Patent: Sep. 2, 2014

(54) COATED METALLIC SAMPLE PEEL TEST

(75) Inventor: Thomas S. Ramotowski, Tiverton, RI (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 630 days.

(21) Appl. No.: 12/894,997

(22) Filed: Sep. 30, 2010

(65) Prior Publication Data

US 2011/0016961 A1    Jan. 27, 2011

Related U.S. Application Data

(62) Division of application No. 11/828,412, filed on Jul. 26, 2007.

(51) Int. Cl.
     *G01N 17/00*        (2006.01)

(52) U.S. Cl.
     CPC ................................ *G01N 17/002* (2013.01)
     USPC ..................... 73/150 R; 204/196.06; 204/404

(58) Field of Classification Search
     USPC .............. 204/196.01–196.07, 196.1, 196.21,
               204/196.34, 196.36, 401, 404; 324/71.1,
           324/72, 72.5, 658, 661, 663, 681–683, 686;
                                            73/150 R
     See application file for complete search history.

(56) References Cited

U.S. PATENT DOCUMENTS

| | | | | |
|---|---|---|---|---|
| 5,213,589 A | * | 5/1993 | Ronning et al. | ................. 51/293 |
| 5,354,600 A | * | 10/1994 | Fisher et al. | ................. 428/215 |
| 5,369,370 A | * | 11/1994 | Stratmann et al. | ............ 324/663 |
| 7,141,150 B1 | | 11/2006 | Welch et al. | |
| 2004/0209100 A1 | * | 10/2004 | Lefebvre et al. | .............. 428/515 |

OTHER PUBLICATIONS

ASTM C794-06 "Standard Test Method for Adhesion-in-Peel of Elastormeric Joint Sealants" Sep. 2006.*

* cited by examiner

*Primary Examiner* — Susan D Leong
(74) *Attorney, Agent, or Firm* — James M. Kasischke; Michael P. Stanley

(57) ABSTRACT

A method for conducting a peel test of a polymer coated metallic sample includes making a peel test specimen having a polymer joined to a substrate. A free portion of the polymer is left unattached to the substrate. The peel test specimen is positioned in an environment for testing in such a manner that the polymer is allowed to peel downward from the substrate. A weight is joined to the free portion of the polymer and a start time is recorded. The attached portion of the polymer is periodically measured and the elapsed time is recorded. A peel rate is calculated from the measurement and time.

7 Claims, 4 Drawing Sheets

COATED METALLIC SAMPLE PEEL TEST

This is a divisional application of U.S. Utility application Ser. No. 11/828,412 filed 26 Jul. 2007. The application by the inventor, Thomas S. Ramotowski is entitled "Coated Metallic Sample Peel Test".

The invention described herein may be manufactured and used by or for the Government of the United States of America for governmental purposes without the payment of any royalties thereon or therefore.

CROSS REFERENCE TO OTHER PATENT APPLICATION

None.

BACKGROUND OF THE INVENTION (1) Field of the Invention

The present invention relates to a material testing method for polymers bonded to metals and, more particularly, to a test for cathodic delamination of such materials in water.

(2) Description of the Prior Art

Many of the metal-polymer bond failures that occur in the marine environment are caused by a process referred to as "cathodic delamination." Cathodic delamination is believed to result from the following reaction on a cathodically polarized surface exposed to seawater:

$$2H_2O + O_2 + 4e^- \rightarrow 4OH^- \qquad (1)$$

FIGS. 1 and 2 show a diagram of cathodic delamination. A material 10 is shown having a cathodically polarized metal substrate 12 with a polymer coating 14. Substrate 12 can be any cathodically polarized metal. Polymer coating 14 can be any polymer coating such as an encapsulant, paint or any other material that adheres to the surface of substrate 12. Material 10 is positioned in an aqueous environment 16.

The standard model for cathodic delamination proceeds as follows: water and dissolved oxygen in aqueous environment 16 diffuse through the polymer layer 14 and reach the underlying cathodically polarized metal surface 12. (Cathodic polarization is a commonly used method for imparting corrosion resistance to otherwise susceptible metals). Once there, the water and oxygen react with each other and with electrons 18 from the metal 12 to generate hydroxide ions at the metal/polymer interface 20. Once hydroxide ions are formed, additional water diffuses to the interface region because of osmotic pressure. In effect, the incoming water is trying to eliminate the concentration gradient for hydroxide ion between the metal/polymer interface region (pH≈14) and the surrounding water (pH≈8). The osmotic pressure differential causes formation of pressurized water-filled "blisters" 22 along the metal-polymer interface 20. When the internal pressure within the blister 22 exceeds the bond strength between the metal and polymer, the bond ruptures in that region.

Repeated millions of times at a very small scale, this process greatly weakens, and eventually eliminates, the bond between the metal and the polymer. If the polymer in question is paint, then the paint will blister and flake off exposing the underlying metal. If the polymer is an encapsulant protecting underlying electrical circuitry or devices, then catastrophic failure can result from exposure of vulnerable parts to seawater. Cathodic delamination is thought to be the major cause of polymer-metal bond failures in the marine environment. The cost of this process to the Navy is on the order of tens to hundreds of millions of dollars per year.

Commercial maritime interests and the Navy are keenly interested in designing and utilizing hardware that is as resistant to cathodic delamination as possible. One of the most commonly employed methods for determining cathodic delamination resistance is the saltwater accelerated life test (ALT). Such a test, if set up and run properly, allows an item of hardware to be artificially aged at a much faster rate in the laboratory than in real life. This allows the test engineer to predict the useful service life of the item under conditions conducive to cathodic delamination (i.e., "worst-case" scenario). Accelerated life tests can also be used to compare how well different materials resist cathodic delamination.

An accelerated life test is typically designed in accordance with the following equation:

$$RAF = e^{\frac{-E_a(T_2-T_1)}{R(T_2 T_1)}} \qquad (2)$$

In this equation, "RAF" is the reaction acceleration factor; "e" is the base of the natural logarithm system; "$E_a$" is the activation energy for the process; "R" is the gas constant; "$T_2$" is the temperature at which the accelerated life test is run; and "$T_1$" is the normal operational environmental temperature for the item in question. Usually $T_2$ is greater than $T_1$ because the speed of most chemical reactions increases with temperature. Thus, by increasing the temperature in the accelerated life test, the rate of the cathodic delamination process can be sped up many-fold, allowing a relatively short duration laboratory test to simulate the equivalent of many years of exposure to normal conditions. The extent to which the higher temperature, $T_2$, has sped up the reaction is indicated by the reaction acceleration factor. For example, if the reaction acceleration factor for a given accelerated life test set up is calculated to be "12", that means the reaction will proceed twelve times faster at $T_2$ than at $T_1$. Thus, one month of exposure to the test conditions at $T_2$ is equivalent to twelve months of exposure at $T_1$. The key variable for determination of the reaction acceleration factor for a given set of temperatures is the activation energy, $E_a$, for the degradative reaction of interest. $E_a$ is akin to an energy barrier that must be surmounted by reactants before a reaction can take place. The higher the $E_a$ value, the slower (in general) the reaction proceeds at room temperature. Unfortunately, $E_a$ is often unknown for a given material or set of materials and, therefore it must be determined experimentally.

Because water and oxygen need to diffuse through the polymer layer to trigger cathodic delamination under the standard model, all standard cathodic delamination accelerated life tests assume the $E_a$ of interest is that for the diffusion of water into the polymer. This view is also re-enforced by the fact that, according to the prevailing model, water must continue to diffuse through the polymer and build up pressure in the interfacial blisters to trigger the actual delamination or debonding. This $E_a$ value is typically calculated by first measuring water diffusion constants at three different temperatures for the polymer in question, and then relating them to the Arrhenius equation (the equation from which equation (2) is derived). One problem that develops concerns the numerical value of $E_a$. If it is low, the reaction in question occurs readily at temperature $T_1$, and the reaction acceleration factor calculated using reasonable values for $T_2$ is small. It should be noted that as $T_2$ is increased, reactions that occur very slowly (if at all) at $T_1$ can be accelerated to such an extent that they have significant effects on the materials being tested. This process can lead to erroneous conclusions from an accelerated life test, because if one is not careful, the observed deterioration may be the result of a process or reaction that occurs only at high temperatures (and thus, would not affect the materials of interest under normal environmental conditions). The problem is conducting a meaningful accelerated life test on a material with a low $E_a$ for water diffusion and thus, a low reaction acceleration factor.

SUMMARY OF THE INVENTION

One object of this invention is to test for cathodic delamination of an object.

Another object of this invention is to provide a method for testing cathodic delamination at an accelerated rate.

Another object of this invention is calculation of activation energy in a model independent manner.

Accordingly, there is provided a method for conducting an accelerated life test of a polymer coated metallic sample. This method includes placing the sample below the water surface in a test tank containing water and an oxygen containing gas. Cathodic polarization of the metallic portion of the sample is increased. This can be achieved by using a voltage source or a sacrificial anode. Dissolved oxygen in the test tank water is also increased. Dissolved oxygen can be increased by providing oxygen under pressure to the tank or through an aerator under the water surface. Temperature can also be regulated to accelerate the test speed. Delamination of the sample is periodically tested. The invention also provides a reaction model independent method for calculating activation energy.

BRIEF DESCRIPTION OF THE DRAWINGS

These and other features and advantages of the present invention will be better understood in view of the following description of the invention taken together with the drawings wherein.

DETAILED DESCRIPTION OF THE INVENTION

Figure 1:
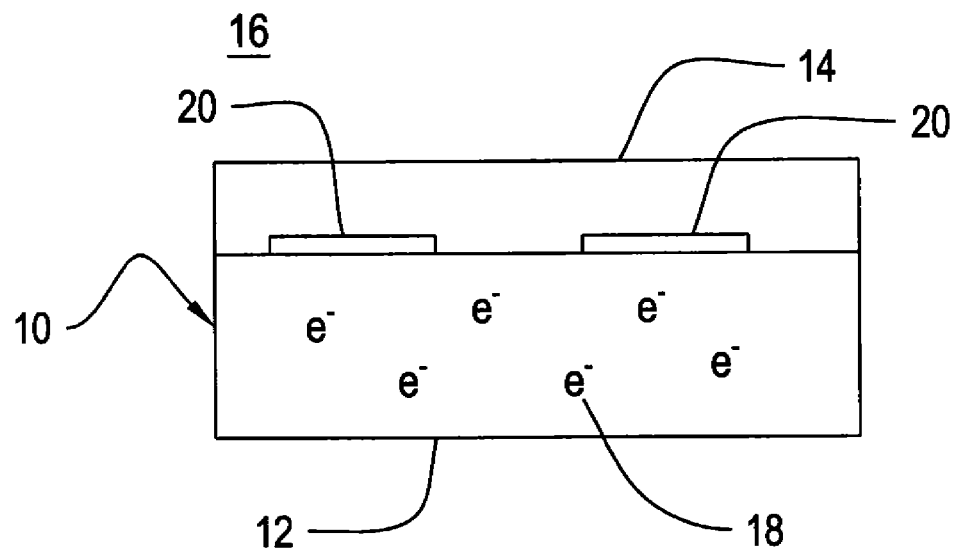
FIG. 1 is diagram showing the first stage of cathodic delamination.
Figure 2:
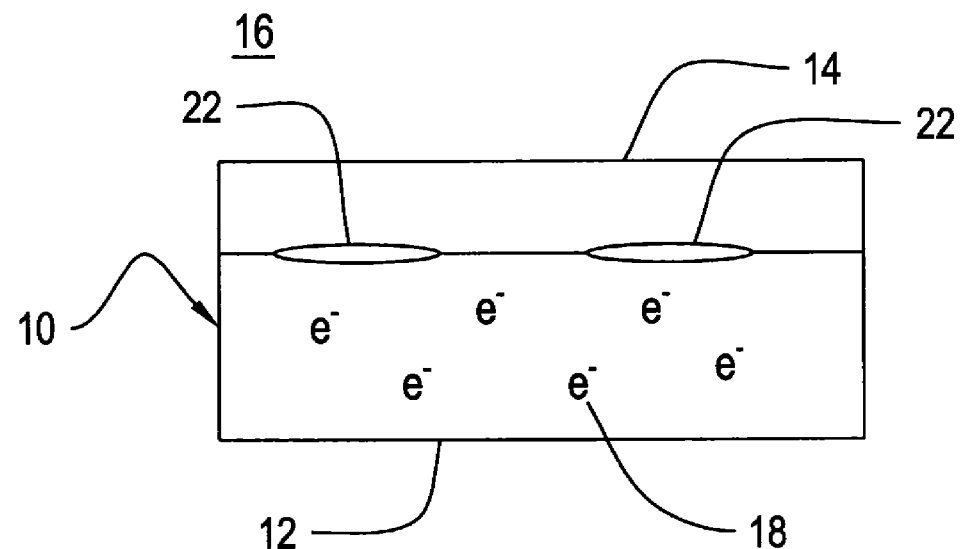
FIG. 2 is diagram showing the later stages of cathodic delamination.
Figure 3:
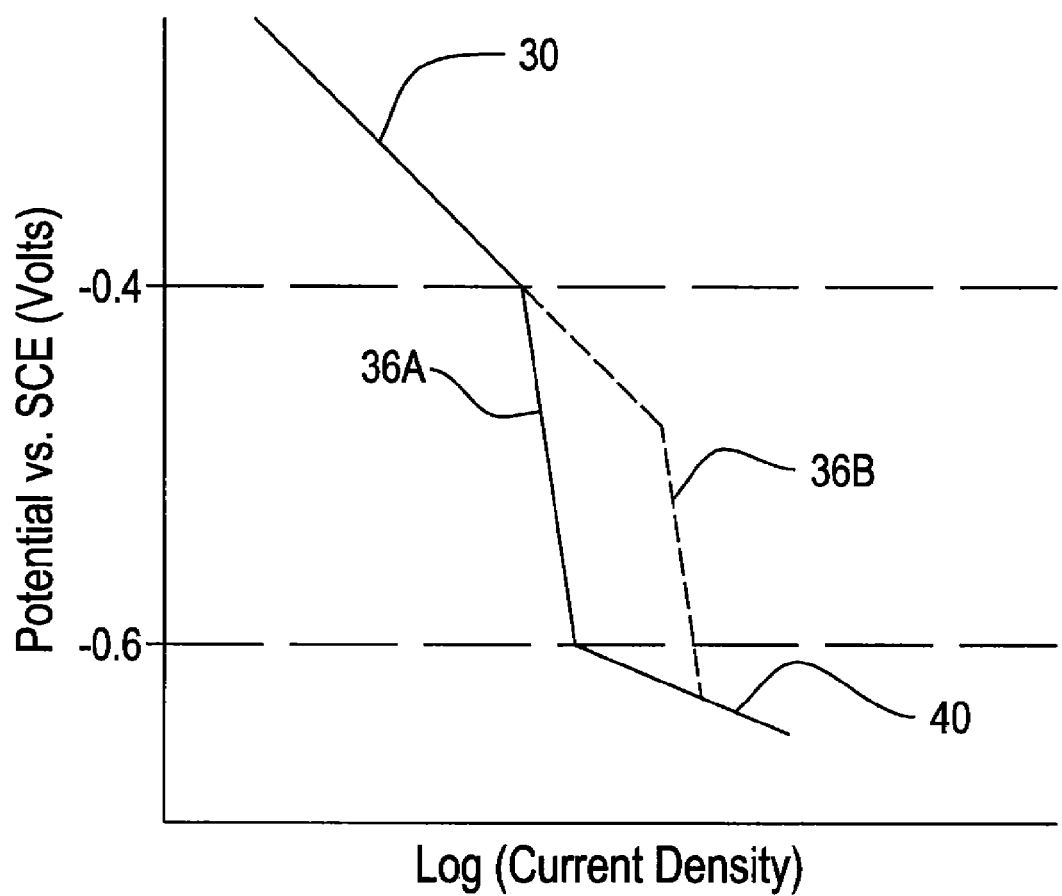
FIG. 3 is graph of electrical potential versus log current density for a cathodic delamination sample.

FIG. 3 shows the general relationship between voltage and current for a corrosion reaction. The cathodic delamination reaction is a corrosion reaction that occurs on a cathodically polarized surface, so it follows this general relationship. As can be seen in FIG. 3 region 30, as polarization (voltage) becomes more cathodic, the current consumed increases. Voltage is measured versus a standard calomel electrode (SCE). Because current consumed is directly proportional to the rate of the corrosion reaction, this means that the reaction rate increases as the polarization becomes more cathodic. However, FIG. 3 also shows that at some potential, region 36A, the current consumed does not change much as the cathodic potential is further increased. In region 36A, the reaction is considered to be "diffusion limited"—i.e., there are insufficient reactants (water and oxygen) on the cathodically polarized surface to support an increase in reaction rate. The available water and oxygen are already reacting, so adding additional electrons no longer increases the speed of the reaction. In region 40, there is a further increase in current where, in a new reaction, hydrogen evolution begins according to the following reaction:

$$2H^+ + 2e^- \rightarrow 2H \rightarrow H_2 \qquad (3)$$

This invention disclosure proposes a method by which the diffusion-limited region 36A of the potential/current graph can be pushed further down in voltage. It is based on increasing the amount of oxygen available for the reaction. After adding oxygen, the potential/current graph extends to the dashed line. This method assumes that oxygen is the reaction-limiting species for the cathodic delamination process. There is much less oxygen available because so little oxygen dissolves in water in the first place (a few parts-per-million or "ppm"). There is plenty of water (the items being tested are submerged in water) and changing the potential provides additional electrons of sufficient voltage to participate in the reaction. The only reactant in short supply is oxygen. The diffusion limited region 36A on FIG. 3 is actually a region where oxygen demand exceeds oxygen availability. If the amount of dissolved oxygen in the accelerated life test tank water can be increased, the potential at which the diffusion limited region occurs will drop as shown by dashed line at 36B, and, therefore, an increase in cathodic polarization will speed up the accelerated life test to a greater extent than is now possible.

The method by which dissolved oxygen in water may be increased results from Henry's Law. The amount of dissolved oxygen in water obeys the following relation (Henry's Law):

$$y_i P = x_i H_i \qquad (4)$$

where "$y_i P$" is the partial pressure of species i, and $H_i$ is Henry's constant for species i. Thus, increasing the partial pressure of oxygen in the accelerated life test tank headspace (above the water) will increase $x_i$, the amount of oxygen dissolved in the water. If all of the gas above the water in the accelerated life test tank is pure oxygen, then the left side of the equation becomes equal to the total pressure of gas in the headspace. It should be noted that $H_i$ for oxygen is fairly large (44,380 bars at 25° C.), so large pressures are necessary to induce significant changes in $x_i$. On the other hand, at 25° C. and 1.0 bar, $x_i$ is so small that easily achieved increases in oxygen gas pressure can result in $x_i$ increasing by a factor of 10. If the expected reaction acceleration factor from temperature increases alone is only on the order of 2 (for reasonable values of $T_2$), an increase of the reaction acceleration factor to 10 or so by the application of Henry's Law can be quite significant and results in a much shorter duration for the accelerated life test.

Figure 4:
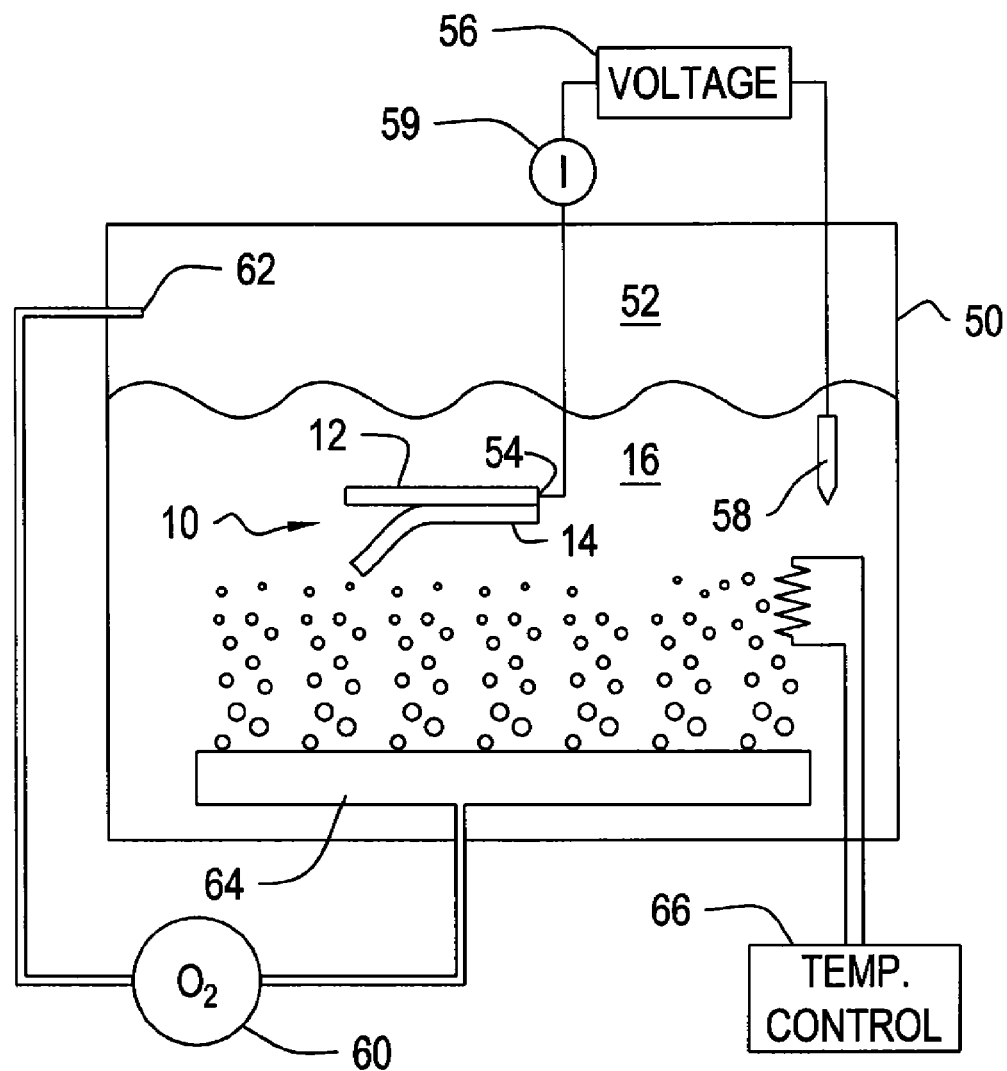
FIG. 4 is a diagram of the test setup of the current invention.

FIG. 4 shows a test setup according to the current invention. A test tank 50 is provided with water 16 and a gas 52 over the top of the water. Test tank 50 is preferably airtight to prevent leakage of gas 52 and water 16. Water 16 can be either fresh water or sea water. According to a first embodiment of the invention, gas 52 has a greater percentage of oxygen than standard air. This percentage can be increased to all oxygen. Sample 10 is positioned under the water 16. An electrode 54 is joined to sample 10 to increase its cathodic polarization. Cathodic potential can be provided via a controlled voltage source 56 with an anode 58 positioned in the water 16. An ammeter can be used to monitor the current to the sample. The current can be used to determine the reaction speed. Electrode 54 should provide a cathodic potential of less than 0.6 volts versus a standard calomel electrode. A simpler, but less controlled, apparatus can be achieved by joining a sacrificial zinc anode to the metal 14 in place of the electrode 54, voltage source 56 and anode 58.

In alternate embodiments, further changes to the test setup can be made to enhance reaction rate. The partial pressure of oxygen in test tank 50 can be increased by joining an oxygen source 60 to the tank 50. Oxygen can be provided either through an inlet 62 above the surface of the water or an inlet such as aerator 64 below the surface of the water. In operation, aerator 64 introduces oxygen bubbles below water surface for better diffusion into water 16. Gas pressure can be any pressure below 10 atmospheres; however, at higher pressures great care must be taken to prevent inadvertent, spontaneous reactions between the oxygen and organic materials within the test tank 50. As a final alternative, a temperature control device 66 is positioned in the water 16. Water temperature can be adjusted to maximize the reaction rate; however, maximum operating temperature is 150° F. to avoid undesirable reactions.

Once exposed to the test conditions, the sample can be tested periodically to determine the extent of cathodic delamination. This can be performed by an American Society for Testing and Materials (ASTM) peel test or another test for determining the strength of the polymer/material bond over time.

Figure 5:
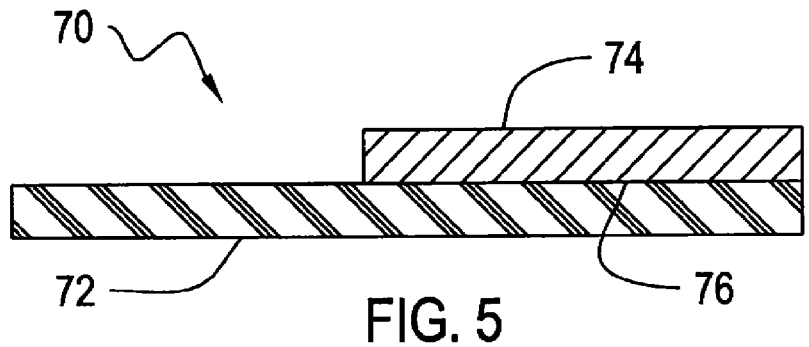
FIG. 5 is a cross sectional diagram of an ASTM peel test sample.

The following discusses a method of using a peel test and calculation of activation energy through such a method. FIG. 5 shows a standard ASTM peel test sample 70 for use in this method. A polymer 72 is bonded to a substrate of interest 74 at a bonding region 76. The polymer 72 extends beyond the substrate 74. In an ASTM peel test sample the polymer 72 is 12 in. and the substrate 74 is 6 in. When used for testing cathodic delamination the substrate 74 is a metal.

Figure 6:
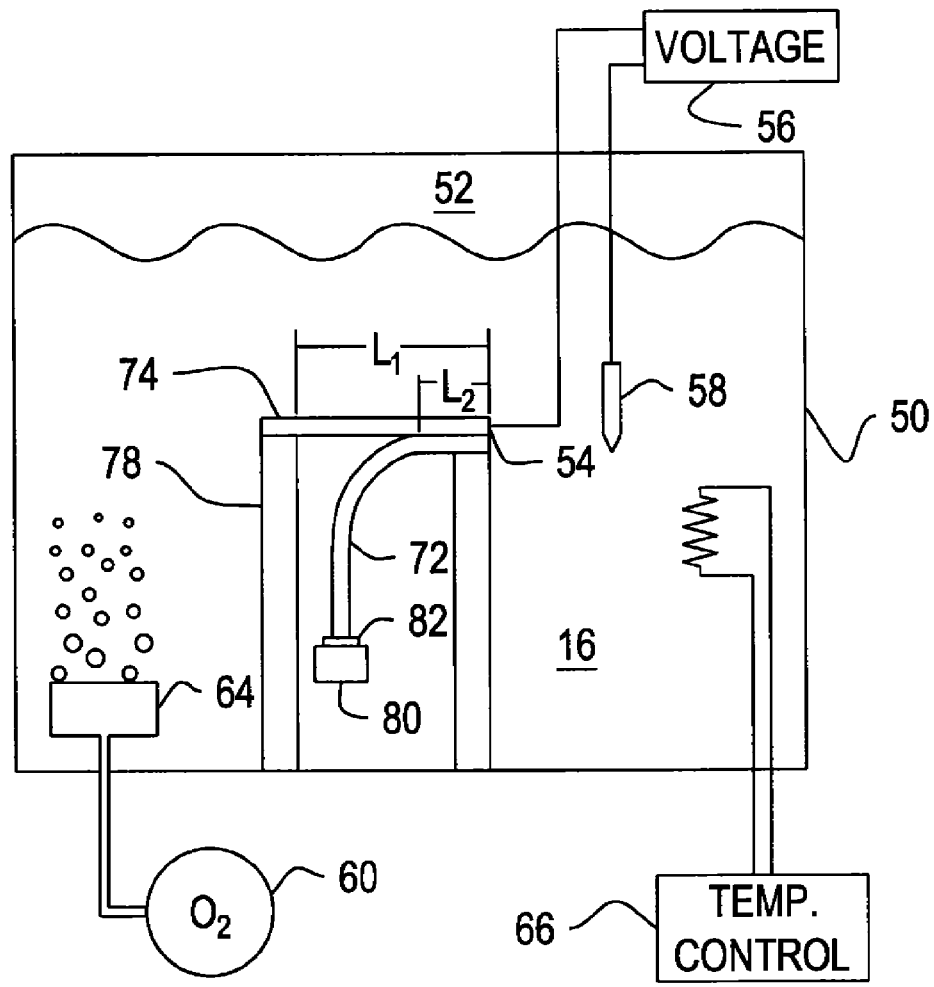
FIG. 6 is a diagram of the test setup of the current invention using a peel test specimen.

FIG. 6 shows the test method of the current invention using a peel test. This test set up is essentially the same as that shown in FIG. 4. In this test, a rack 78 is provided for holding multiple samples 70. As shown in FIG. 5, sample 70 has portion polymer 72 which is not bonded to substrate 74. Samples 70 are positioned on rack 78 so that the polymer 72 is free to peel downward from substrate 74. The portion of polymer 72 not bonded to substrate 74 is identified as the free portion. The length of completely bonded polymer, $L_1$, should be measured and recorded at the beginning of the test. Sample 70 and rack 78 are placed in tank 50 with the sample 70 fully immersed in water 16. A cathodic voltage source such as a battery or sacrificial zinc anode is electrically connected to sample 70 to impart the proper cathodic voltage to encourage cathodic delamination. Pure oxygen can be bubbled through the water to ensure an adequate supply of dissolved oxygen is maintained at all times. This can be done by oxygen source 60 and aerator 64. Once the sample or samples 70 are completely submerged, 5-pound weights 80 are attached by thumb-clamps 82 to the polymer 72 hanging down from the substrate 74. As the test is being conducted, weight 80 will pull free portion of polymer 72 downward, and polymer 72 will become debonded from substrate 74. The initial length of the bonded region is shown as $L_1$. As the test goes on the length of the bonded region becomes $L_2$. The length of the completely-bonded substrate, $L_2$, can be measured periodically. A debonding rate can be calculated as the difference between the initial length $L_1$ of the bonded region and the measured length $L_2$ divided by the elapsed time.

A cathodic delamination accelerated life test can be conducted by adding a cathodic polarization means, an oxygen source and a temperature control means to the test set up. In this type of test, substrate 74 is metallic. The cathodic polarization means includes electrode 54, voltage source 56 and anode 58 joined to specimen 70 to increase its cathodic polarization. As discussed previously, electrode 54 should provide a cathodic potential of less than 0.6 volts versus a standard calomel electrode. A simpler, but less controlled, apparatus can be achieved by joining a sacrificial zinc anode to substrate 74 in place of the electrode 54, voltage source 56 and anode 58.

Another means of speeding up the test includes providing an oxygen source 60 in communication with the water 16 in tank 50 through an aerator 64. This increases the percentage of oxygen supporting the cathodic delamination reaction. The reaction can also be accelerated by increasing the pressure of oxygen above water 52. As a final alternative, a temperature control device 66 is positioned in the water 16. Water temperature can be adjusted to maximize the reaction rate; however, maximum operating temperature is 150° F. to avoid undesirable reactions.

Activation energy, $E_A$, can be calculated by performing the test of FIG. 5 at two or more different temperatures. Peel rates can be obtained at each temperature. By assuming that the debonding follows the Arrhenius equation:

$$PR = ke^{-\frac{E_A}{RT}} \qquad (5)$$

where:
PR=peel rate,
k is a constant,
R is the gas constant, and
T is the absolute temperature in Kelvins of the test.
By taking the natural logarithm of both sides of the equation, one obtains:

$$\ln(PR) = -\frac{E_A}{RT} + \ln(k) \qquad (6)$$

Thus a plot of ln(PR) versus 1/T should be linear, and the slope of the resulting line should be equal to $-E_A/R$. Since R is a well known constant, the activation energy, $E_A$, can be easily calculated. This gives a model independent value for the activation energy of the cathodic delamination reaction that does not require derivation from the diffusion model.

In light of the above, it is therefore understood that within the scope of the appended claims, the invention may be practiced otherwise than as specifically described.

What is claimed is:
1. A method for conducting a peel test of a polymer coated metallic sample comprising the steps of:
making a peel test specimen having a polymer joined to a substrate wherein an attached portion of said polymer is joined to said substrate and a free portion of said polymer is not attached to said substrate, a bonding region being present between said polymer and said substrate;
providing an environmental test chamber capable of controlling an environment for testing;
supporting said peel test specimen horizontally in the environment for testing in such a manner that said polymer is allowed to peel vertically downward from said substrate;
joining a weight to said free portion of said polymer subjecting the bonding region to vertically downward tension at a region subject to the environment for testing;
recording a start time when said weight is joined to said polymer;

periodically measuring said attached portion of said polymer and said elapsed time from said recorded start time; and calculating a peel rate as a ratio of distance to time from said attached portion measurement and said elapsed time.

2. The method of claim 1 wherein said peel test specimen is an ASTM peel test specimen.

3. The method of claim 1 wherein said peel test specimen is supported by a frame.

4. The method of claim 1 wherein said substrate is metal.

5. The method of claim 4 further comprising the step of cathodically polarizing said substrate.

6. The method of claim 5 further comprising increasing the oxygen content of said environment for testing.

7. The method of claim 6 further comprising raising the temperature of said environment for testing.

* * * * *